United States Patent
Klimova

(10) Patent No.: US 9,468,682 B2
(45) Date of Patent: Oct. 18, 2016

(54) COMPOSITIONS AND METHODS FOR ENHANCING PENETRATION OF BIOLOGICALLY ACTIVE SUBSTANCES INTO TISSUES OR ORGANS

(71) Applicant: Joint-stock company "High Tech", Saint-Petersburg (RU)

(72) Inventor: Olga Klimova, Moscow (RU)

(73) Assignee: Joint-stock company "High Tech", Saint-Petersburg (RU)

( * ) Notice: Subject to any disclaimer, the term of this patent is extended or adjusted under 35 U.S.C. 154(b) by 0 days.

(21) Appl. No.: 13/857,735

(22) Filed: Apr. 5, 2013

(65) Prior Publication Data

US 2014/0302142 A1    Oct. 9, 2014

(51) Int. Cl.
| | |
|---|---|
| *A61K 47/02* | (2006.01) |
| *A61K 31/728* | (2006.01) |
| *A61K 38/22* | (2006.01) |
| *A61K 38/44* | (2006.01) |
| *A61K 9/00* | (2006.01) |
| *A61K 31/7088* | (2006.01) |

(52) U.S. Cl.
CPC ............... *A61K 47/02* (2013.01); *A61K 9/006* (2013.01); *A61K 9/0014* (2013.01); *A61K 31/7088* (2013.01); *A61K 31/728* (2013.01); *A61K 38/446* (2013.01); *C12Y 115/01001* (2013.01)

(58) Field of Classification Search
None
See application file for complete search history.

(56) References Cited

U.S. PATENT DOCUMENTS

| | | | |
|---|---|---|---|
| 7,384,918 | B2 | 6/2008 | Graham |
| 2005/0244485 | A1 | 11/2005 | Hsu et al. |
| 2011/0178044 | A1 | 7/2011 | Hsu et al. |
| 2011/0190688 | A1* | 8/2011 | Tagliaferri et al. ............. 604/20 |
| 2012/0213837 | A1* | 8/2012 | Botchwey, III ............... 424/423 |

FOREIGN PATENT DOCUMENTS

| | | |
|---|---|---|
| EP | 804155 B1 | 11/2000 |
| RU | 2411045 | 3/2009 |
| RU | 2462265 | 9/2012 |

OTHER PUBLICATIONS

Fermencol http://www.hmesil.kiev.ua/index.php?option=com_content&view=article&id=78&Itemid=132&lang=en.*

John W. Gronwald et al., Effect of Ammonium Sulfate on Absorption of Imazethapyr by Quackgrass (Elytrigia repens) and Maize (Zea mays) Cell Suspension Cultures, Weed Science (1993) 41:3, 325-334.

* cited by examiner

*Primary Examiner* — Robert A Wax
*Assistant Examiner* — Danah Al-Awadi
(74) *Attorney, Agent, or Firm* — McCarter & English LLP; Steven G. Davis

(57) ABSTRACT

According to this invention, compositions and methods for increasing the extent of penetration of a biologically active substance into the tissues and organs are proposed, the methods comprising administration of the biologically active substance in combination with one or more chaotropic agents, e.g., ammonium sulfate.

17 Claims, 1 Drawing Sheet

Insulin diffusion profiles with ammonium sulfate in donor/ acceptor solutions.
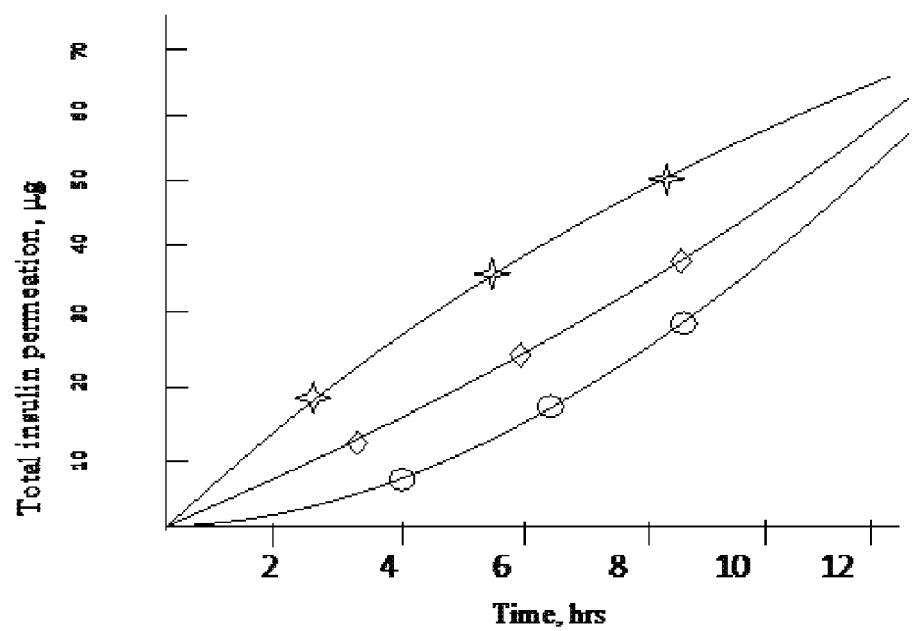
○ - 3 mM ammonium sulfate,
◇ - 5 mM ammonium sulfate,
✧ - 20 mM ammonium sulfate

COMPOSITIONS AND METHODS FOR ENHANCING PENETRATION OF BIOLOGICALLY ACTIVE SUBSTANCES INTO TISSUES OR ORGANS

FIELD OF THE INVENTION

The present invention relates to the field of medicine, more specifically to the delivery of biologically active substances, including enhancement of transdermal and transmucosal delivery, such as transbuccal delivery of biological agents.

BACKGROUND OF THE INVENTION

A lot of drugs of the new generation, primarily proteins, including recombinant proteins, and many other substances are not intended for administration using oral, inhalation and nasal routes. The drug delivery by means of injections is also not quite applicable; such proteins as, for example, interferons, interleukins and insulin rapidly get cleared out of the blood system and undergo proteolysis, including autolysis, tend to aggregate, adsorb and denature. Transdermal and transmucosal/transbuccal methods could be the most convenient routes to deliver these substances, all the more so transdermal and transmucosal/transbuccal delivery is much easier than the use of injections.

Theoretically, skin and mucous membranes can be viewed as a convenient route for the painless topical and systemic administration of multiple drug substances, but in practice the skin and mucous membranes act as a barrier, preventing penetration from the outside as well as the loss of water, electrolytes and resist the effects of chemical, physical and biological agents. Currently very few drug substances are delivered into the patients' bodies transdermally in clinical settings due to the low permeability of skin and mucous membranes.

The effectiveness of transdermal and transmucosal/transbuccal delivery of biologically active substances depends on their ability to penetrate skin and mucous membranes in the therapeutically effective amounts.

Maximum passive permeability through the concentration gradient-driven diffusion exists and is proved for the low molecular weight substances. However the diffusion through the skin of the large, particularly hydrophilic, molecules (molecular weight>500 kDa) is extremely low due to the skin (and mucous membranes) structure, primarily because of the outermost corneous skin layer—stratum corneum (SC). At the same time, many biopolymers, especially peptides and proteins, are effective therapeutic agents; however their delivery into the body through diffusion is practically impossible due to the fact that most of biologically active substances are not able to penetrate the barrier formed by the skin and mucous membranes. This is due to the physical and chemical properties of these substances. The majority of peptides, proteins and other biopolymers are high molecular weight hydrophilic substances that are not able to passively penetrate the mucous membranes and skin, especially the stratum corneum, the top layer of skin, as well as the underlying layers of skin and membranes, which only allow the molecules of low molecular weight lipophilic substances to pass through. For example, permeation efficiency of the charged substances through the stratum corneum is by two orders of magnitude lower than the permeation efficiency of the un-charged ones.

Methods of increasing skin permeability such as iontophoresis, microinjections, electroporation, sonophoresis, etc. allow transdermal and transmucosal/transbuccal delivery of large charged molecules, including peptides and proteins, which cannot pass through the stratum corneum and membranes by means of passive diffusion. The main advantages of these methods are a rapid onset of the drug action due to a short time period required for the pharmaceutical/cosmetic agents to reach their target, and also the ability to control the delivery by varying the strength and duration of exposure. Among the disadvantages are the patient's low compliance rate and contraindications for use of instrumental methods of drug delivery in a number of diseases.

Special substances that are called penetration enhancers (penetrators) are applied with a goal of reducing the impermeability of body barriers. Such substances facilitate the transdermal and transmucosal/transbuccal delivery of drug substances.

Many potential enhancers and technologies for transdermal delivery improvement are known, but, for a number of reasons, their efficiency is not satisfactory.

For instance, the early enhancers (for example, dimethyl sulfoxide and dimethyl formamide) were keratolytic agents. They irreversibly destroyed SC and accelerated skin penetration of a wide range of substances.

The serious drawbacks of such substances were toxicity, irritating properties and odor. Moreover, irreversible destruction of SC is not desirable.

The recently discovered enhancers, including propylene glycol, alcohols, surfactants and the like, whose application has fewer drawbacks, act by increasing the fluidity of the stratum corneum lipids. However, their effect is not sufficient for the effective transdermal delivery of biopolymers (Ashok K. Tiwary et al. 2007). Correspondingly, according to the well-known "500 Daltons rule", even when using the chemical enhancers, the transdermal delivery of large (>500 Da) hydrophilic molecules through the intact skin into the bloodstream is almost impossible (Bos J. D. et al. 2000).

Another issue associated with the application of natural or recombinant biopolymers as the active agents relates to their stabilization during storage and use. First of all, this refers to peptides and proteins, particularly proteolytic enzymes, due to their rapid degradation caused by proteolysis and autolysis, which are the major obstacles to their use in medicine and cosmetology. In order to reduce the degradation of peptides they are stored as a dried powder and reconstituted before use.

It is desirable to produce ready-to-use forms since it will not require the assistance of highly qualified personnel during their application and increase the dosage precision.

At the same time it is necessary that the high-purity natural or recombinant biopolymers preserve their intact structural and functional properties for a long storage period, i.e. from several weeks up to several years in the ready-to-use forms. Thus, during the storage period, the molecules of the pharmaceutical/cosmetic products should be therapeutically and, ideally, biochemically inactive (which is particularly important in case of proteolytic enzymes).

If a modified polypeptide is used in order to achieve this goal, it is required to ensure that upon reaching the target, the modified molecules reinstate their original structure, thereby restoring their therapeutic properties.

It is obvious that the advances in the search for substances, which would allow overcoming these limitations, will significantly push forward towards the creation of the effective systems for transdermal and transmucosal/transbuccal delivery of the biologically active substances and expand the field of their application.

SUMMARY OF THE INVENTION

Therefore, the objective of this invention is to develop new means of delivery of a wide range of biologically active substances, including biopolymers, so that these substances ensure the efficient delivery of the effective agent and preferably are ready for use.

This objective is reached by proposing a composition for transdermal and transmucosal delivery, including transbuccal delivery, comprising one or more biologically active substances, ammonium sulfate and pharmacologically acceptable excipients.

This invention also provides a composition for transdermal and transmucosal delivery, including transbuccal delivery, of insulin, the composition comprising insulin, ammonium sulfate and pharmacologically acceptable excipients. The aforementioned composition may be in a form of a solution, mixture, suspension, gel, sol, aerosol, paste, ointment, liniment, cream, powder, pill, coated pill, granule, capsule, suppository, patch and skin glue.

This invention also provides means of transdermal and transmucosal treatment, including transbuccal treatment, by administering biologically active substances to a subject in need of this treatment, wherein the skin and mucous membranes of the subject is contacted with the aforementioned biologically active substances in combination with ammonium sulfate.

This invention also provides a method to increase the extent of penetration into the tissues and organs of a subject in need of treatment by the biologically active substance, wherein the administration of an effective amount of the aforementioned biologically active substance is carried out in combination with ammonium sulfate. This method allows the delivery into scars, contractures and joint cavities by means of injections while the biologically active substance can be a proteolytic, in particular, collagenolytic, enzyme.

This invention also provides a method to increase the extent of penetration of the biologically active substance into skin and mucous membranes of a subject in need of the treatment, wherein skin and mucous membranes of the subject are contacted with an effective amount of the aforementioned biologically active substance in combination with ammonium sulfate.

The biologically active substances applied in the mentioned methods can be biopolymers, including peptides, proteins and oligonucleotides, e.g. enzymes.

This invention also provides a method for transdermal and transmucosal delivery, including transbuccal delivery, of insulin to a subject in need of insulin administration, wherein the skin and mucous membranes of the subject are contacted with an effective amount of insulin in combination with ammonium sulfate.

The mentioned methods provide for dermal, buccal, sublingual, rectal, urethral, vaginal, oral delivery and delivery by means of inhalation and instillation.

In the compositions and methods according to the invention, the ammonium sulfate concentration allows loosening of the structural components of barriers, temporarily reducing the local impermeability of skin and mucous membranes and, simultaneously, transformation of the molecules of the biologically active substances into a more compact form, thus increasing their ability to diffuse through the barriers.

In the compositions and methods according to the invention, the delivery of the biologically active substances to a specified depth is achieved by forming the ammonium sulfate gradient of concentration in the organs and tissues.

The properties of barriers and the delivered biologically active substances are restored after the external action (treatment) has been terminated.

It is reasonable to have the ammonium sulfate concentration in the solution of the delivered substance at 100-0.001% of saturation or at 99.999%-0.0001% in a dry form.

In the compositions and methods according to the invention, the biologically active substances can be biopolymers, e.g. oligonucleotides, peptides, proteins, enzymes in particular, e.g. proteolytic enzymes, or superoxide dismutase, or insulin.

In the compositions and methods according to the invention, the biologically active substances can be substances used in mesotherapy.

This invention also provides a method for increasing dermal or mucosal permeability to one or more biologically active agent in a subject in need of treatment with the biologically active agent, comprising contacting dermal tissue or mucosal tissue with an effective amount of the one or more biologically active agent in combination with one or more chaotropic agent.

Further provided is a method of transdermally or transmucosally treating a subject with one or more biologically active agent who is in need of treatment with the agent, comprising contacting dermal or mucosal tissue of the subject with one or more biologically active agent in combination with one or more chaotropic agent.

The chaotropic agent may comprise an ion selected from the group consisting of a citrate, a sulfate, a phosphate, a chloride, a nitrate and a thiocyanate. In one embodiment, the chaotropic agent is ammonium sulfate.

The biologically active agent may be a biopolymer, e.g., an oligonucleotide, a protein, a peptide or an enzyme.

In some embodiments of the methods of the present invention, the subject has diabetes and the biologically active agent is insulin.

In other embodiments of the present invention, the subject has a skin wound or a scar and the biologically active agent is a proteolytic enzyme. The proteolytic enzyme may be collagenase. The collagenase may be represented by a complex of collagenolytic digestive proteases that may be isolated from hydrobionts, e.g. crabs or squids. In some embodiments, the skin wound or a scar may result from a surgery, a burn, a frostbite, acne, contracture or arthritis.

In some embodiments of the methods of the present invention, the dermal tissue is skin. In other embodiments, the mucosal tissue is buccal tissue.

In some embodiments, the biologically active agent is superoxide dismutase.

In some embodiments, the one or more biologically active agent in combination with ammonium sulfate may be administered dermally, bucally, sublingually, transmucosally, rectally, urethrally, vaginally, orally, instillationally or by inhalation. For example, in certain embodiments, the one or more biologically active agent in combination with ammonium sulfate may be administered orally in the form or a tablet, a capsule or a pellet. In other embodiments, the one or more biologically active agent in combination with ammonium sulfate is administered topically in the form of a gel, an ointment, a liniment, a lotion, a cream, a pill, a powder, a solution, a suspension, an emulsion, a suppository, a patch or a skin adhesive. In yet other embodiments, the one or more biologically active agent in combination with ammonium sulfate may be administered by an intradermal injection.

In certain methods provided by the present invention, one or more biologically active agent is used for mesotherapy and is a vitamin, an amino acid or a hyaluronic acid.

BRIEF DESCRIPTION OF THE DRAWINGS

FIG. 1 demonstrates the dependence of the total amount of insulin that passed through the skin on the ammonium sulfate concentration.

DETAILED SPECIFICATION

In the context of this invention, "location where the biologically active substance has been applied" is the location where this biologically active substance immediately contacts the subject's body and can penetrate the tissues and body organs including the skin, mucous membranes, blood, lymph, muscles, joints, to achieve the expected effect. The location where the substance is applied can be a tissue or an organ, e.g.: muscle, mucous membrane, joint cavity and etc. The delivery can be carried out by contact with the skin surface or mucous membrane or by means of injections. Any mode to deliver the effective agent can ensure both topical and resorptive effect.

In the context of this invention, transdermal delivery is the delivery of an active substance or an agent through the skin, wherein the active substance penetrates the intact skin without when it is applied to the skin. The skin penetration by the active substance occurs by itself, e.g., without additional influence, such as an electric field. Accordingly, ionophoretic delivery of the ionized substances through the skin, wherein the absorption of the active agent is ensured by a weak electric field, is not covered by the term "transdermal" delivery herein. Transdermal delivery is carried out by means of ointments, creams, gels, solutions, suspensions, bandages and medical films etc.

Transmucosal delivery is the delivery of an active substance or an agent through mucous membranes, e.g. nasopharynx, intestines, vagina and etc. Transmucosal delivery also occurs with any enteral administration of the effective agent where the effective agent contacts the mucous membranes of a digestive tract. Transmucosal delivery through the mucous membranes of the intestines is carried out by means of solutions, suspensions, gels, suppositories, as well as pills, capsules, pellets which can have enteric coating. Transmucosal delivery includes intranasal delivery which is carried out, for instance, by means of solutions, ointments, and sprays. The delivery of the active agent through the mucous membranes of the oral cavity is covered by the term "transbuccal delivery". Transbuccal delivery includes sublingual delivery. Transbuccal delivery is carried out by means of solutions, suspensions, gels, pills, capsules, pellets, and pastilles, etc.

The delivery of the active substance or an agent can be carried out by means of injections. Skin injection is an intradermal delivery. Injections can be administered to the joint cavity as well as any organs and tissues. Injections can also mean microinjections, as used, for instance, in mesotherapy.

Mesotherapy is a non-surgical cosmetic medicine treatment. Mesotherapy employs multiple injections of pharmaceutical and homeopathic medications, hormones, plant extracts, vitamins, and other ingredients into subcutaneous fat. Alternatively, mesotherapy may involve non-injective, e.g., topical administration, of the pharmaceutical and homeopathic medications as listed above.

In the context of this invention, the "treatment" is targeted at a reversible or irreversible modification of the state of the body or any part of the body with the aim of achieving medical, preventive and cosmetic effect.

Biologically active substance or an agent is a substance or an agent that can reversibly or irreversibly modify the state of the subject's body or any part of the subject's body with the aim of achieving medical, preventive and cosmetic effect. Among the examples of the biologically active substances are insulin, protease, oligonucleotides, vitamins and etc.

The term "collagenase" refers to any enzyme or enzyme preparation that can digest collagen molecules under physiological conditions. This term may refer to any collagenase enzyme, e.g., the enzyme isolated from *Clostridium* sp. Alternatively, this term may also refer to a complex of collagenolytic digestive proteases, e.g., isolated from hydrobionts, such as crabs or squids. This complex may be referred to using any one of the following trade names: Collagenase-K, Polycollagenase or Fermencol. Isolation of the complex was described in Klimova et al., Extraction of enzymes from the hepatopancreas of the Chionoecetes Opilio and their characteristics, The Proceedings of the USSR Academy of Sciences (1991), Vol. 317, No. 2, the entire contents of which are hereby incorporated herein by reference.

Pharmacologically acceptable excipients are the auxiliary substances used to prepare pharmacological formulations, for instance, gels, ointments, liniments, creams, powders, pills, solutions, suspensions, sols, emulsions, suppositories, patches, and skin glues. In particular, these are the non-organic and organic carriers. Lactose, corn starch and the derivatives thereof, talc powder, stearic acid or the salts thereof and etc. can be used, for instance, as such carriers for pills. Appropriate carriers to prepare solutions and syrups are, for instance, water, polyols, sucrose, invert sugar, glucose and etc. Appropriate carriers for suppositories are, for instance, natural and hardened oils, waxes, fats, semi-liquid or liquid polyols and etc. Pharmacologically acceptable excipients also include cosmetically acceptable auxiliary substances. Moreover the compositions according to the invention can contain preservatives, solubilizers, stabilizers, wetting substances, emulsifiers, sweetening agents, coloring agents, flavors, and salts to regulate osmotic pressure, buffers, masking agents or antioxidants, and other required components.

Effective amount means the amount required to achieve the desired effect.

Ammonium sulfate can be used in the amount of 100% to 0.00001% of saturation (which depends on the solvent, temperature, content of other dissolved substances). In case of ammonium sulfate solution in distilled water at room temperature, the saturated concentration is 4.08 M.

"Combined" action results after simultaneous, separate or sequential administration and can occur if the components are combined in one or several dosage forms.

The authors of this invention have discovered an unexpected effect consisting in that ammonium sulfate as a component of the biologically active substance allows the increase in permeability of any body tissue, including skin or mucous membrane, for such biologically active substance, notably, allows transdermal or transmucosal delivery thereof, as well as the enhancement of the effectiveness of the biologically active substance when it is topically applied. Thus, ammonium sulfate acts as a penetration enhancer.

The ammonium sulfate effect was reversible. Notably, after a certain time period after the action of ammonium sulfate is terminated, the initial structure of high molecular weight substances is restored. This allows resolution of the issue related to the creation of penetration enhancer which reversibly affects the body, including the skin and mucous membranes, notably with minimal unwanted side effects.

In the course of extraction and purification of natural and recombinant biopolymers there is a stage that involves salting out with ammonium sulfate Ammonium sulfate is an ionic compound having lyotropic properties. During precipitation of proteins, ammonium sulfate acts in two ways: firstly, sulfate ions make the protein molecule more compact and less soluble due to the interaction with the positively charged amino acids, and secondly, sulfate ions dehydrate the protein molecule, reversibly changing its conformation.

Empirical observations of the proteins' salting out have shown that "open" proteins, which do not have a tight spatial structure, do become more compact and, as a result, their ability to diffuse into intact skin, including SC, increases dramatically. However ammonium sulfate affects not only exogenously delivered substances, but also the components of skin.

Essentially, ammonium sulfate action is a combination of two effects: a chemical effect that increases permeability of SC and subjacent skin layers, as well as mucous membranes, by means of distortion of their regular structure (chaotropic effect); and a biochemical effect that involves reversible structural modification of biologically active substances for their efficient permeation through the skin barrier (kosmotropic effect). Moreover, ammonium sulfate has a stabilizing effect on the biologically active substances, affording ready-to-use forms of the biologically active substances that can be stored for suitable periods of time and are characterized by good quality of preparation.

At a concentration of <0.1 M sulfate ions act as a chaotrope, and at a concentration of >0.2 M sulfate ions act as a kosmotrope, i.e. at a higher ammonium sulfate concentration protein solubility reaches a maximum and then decreases.

Without wishing to be bound by a specific theory, it is believed that when a composition for transdermal and transbuccal delivery is applied to the skin, ammonium sulfate, being a component of the composition, starts to interact with skin proteins; increasing their solubility due to the chaotropic effect and thereby weakening the barrier properties of the skin. At a concentration of <0.1 M, ammonium sulfate increases the entropy in the structure of skin and mucous membranes, making the three dimensional structure of collagen fibrils forming the skin layers and mucous membranes more permeable for transdermally delivered substances. That is, ammonium sulfate sufficiently increases skin permeability for macromolecules, thus weakening the effectiveness of the skin barrier in preventing the diffusion of the high molecular weight (MW>500 kDa) polar chemical compounds. As a result, the topically applied biologically active substances penetrate the skin and the subjacent skin layers.

On the whole, ammonium sulfate does not have any toxic or aggravating effects on the skin and body.

Numerous chaotropic agents will have a similar effect on the structural elements of the skin. A chaotropic agent is an agent that disrupts the structure of, and denatures, macromolecules such as proteins and nucleic acids. Chaotropic agents increase the entropy of the system by interfering with intramolecular interactions mediated by non-covalent forces such as hydrogen bonds, van der Waals forces, and hydrophobic effects. In certain embodiments of the invention, a chaotropic agent is the agent that increases permeability of tissues, such as SC, by reversibly disrupting their structure. A chaotropic agent may comprise a chaotropic ion for instance, citrate, sulfate, phosphate, chloride, nitrate, and thiocyanate, etc. Kosmotropic effect ("salting out" effect) in this series decreases while the chaotropic properties increase.

Ammonium sulfate is an ideal agent due to the combination of its strong chaotropic properties and its reversible modification effect on the exogenously delivered substances. This combination results in synergism that increases local delivery of the biologically active substances by several orders of magnitude.

Ammonium sulfate affects not only collagen fibrils, the structure-forming elements of skin and mucous membranes, but also keratinocytes, which form the stratum corneum. Evidently, the increase in skin hydration level leads to more effective transdermal delivery of both hydrophilic and lipophilic chemical compounds without affecting living cells. It can be assumed that ammonium sulfate increases the level of keratinocyte hydration due to osmotic effects. It loosens both SC by "swelling" its protein structural components and the subjacent skin layers by means of softening the interstitial collagen, thus forming routes in the intercellular space for transdermal delivery of various therapeutic agents.

Table 1 demonstrates the effect of ammonium sulfate at different concentrations by means of "loosening" that increases the Collagen Type I and III availability for proteolytic hydrolysis (exemplified by Fermencol™ that contains a complex of collagenolytic digestive protease from hydrobionts).

TABLE 1

| No. | Ammonium sulfate concentration in proteolytic/ collagenolytic enzyme (Fermencol) solution, mM | Ammonium sulfate final concentration in reaction mix, mM | Specific activity of Fermencol preparation toward Collagen Type I (Collagen Type I, Sigma-Aldrich, No. C9879), Mandl units | Specific activity of Fermencol preparation toward Collagen Type III (Collagen Type III, Sigma-Aldrich, No. C3511), Mandl units |
|---|---|---|---|---|
| 1 | 0 | 0.00 | 125.4 | 188.10 |
| 2 | 50 | 0.50 | 131.8 | 205.61 |
| 3 | 200 | 1.98 | 667.7 | 951.55 |
| 4 | 1000 | 9.90 | 672.4 | 1008.60 |
| 5 | 2000 | 19.80 | 678.2 | 1003.74 |
| 4 | 3000 | 29.70 | 671.3 | 997.98 |
| 5 | 4000 | 39.60 | 679.0 | 1001.64 |

The collagen degradation effect was determined in Mandl units (Mandl I. et al. 1953). The collagenolytic enzymes (10 μg per 1 sample) were incubated with Collagen Type I and Type III for 5 hours. The degradation of collagen was determined by the measuring the concentration of liberated terminal $NH_2$ groups that formed during proteolysis. The concentraton was expressed in μmoles (the calibration curve was based on leucine) per 1 mg of the enzymatic agent. One unit equals one μmol of leucine released from collagen in the course of hydrolysis process during 5 hours at 37° C. and at pH of 7.5, with constant stirring.

The presence in the reaction mix of ammonium sulfate at the concentration over 5 mM results in the tenfold increase in collagen degradation. However, ammonium sulfate does not affect the azocasein hydrolysis (Table 2), which proves the chaotropic effect of ammonium sulfate on collagen fibrils. The rate of azocasein hydrolysis was determined using the standard method (Fernanda Sousa et. al. 2007).

TABLE 2

| | Ammonium sulfate concentration in proteolytic/ collagenolytic enzyme (Fermencol) solution, mM | Ammonium sulfate final concentration in reaction mix, mM | Specific activity of collagenolytic enzyme (Fermencol) solution preparation toward Azocasein (Azocasein, Sigma-Aldrich, A2765), O.D. |
|---|---|---|---|
| 1 | 0 | 0.00 | 112.1 |
| 2 | 50 | 0.50 | 113.2 |
| 3 | 200 | 1.98 | 112.7 |
| 4 | 1000 | 9.90 | 113.0 |
| 5 | 2000 | 19.80 | 112.6 |
| 4 | 3000 | 29.70 | 114.2 |
| 5 | 4000 | 39.60 | 112.9 |

Evidently, an increase in the effectiveness of collagen hydrolysis in presence of ammonium sulfate is connected to the increased availability of collagen as a substrate as a result of loosening of its structure.

Further, we present the experiments on studying the skin permeability for certain biologically active substances.

The experiments on in vitro the skin permeability in the presence of ammonium sulfate were carried out at 37° C. using Franz diffusion cell based on the method of Shiow-Fern Ng. et. al. 2010. The vertical Franz diffusion cell was used (PermeGear, Bethlehem, USA) with the effective diffusion surface of 2 cm$^2$.

The experiments were carried out using the skin of male species of Sprague-Dawley rats, weight 110-120 g, taken from the front abdominal wall. Hair and adipose tissue were removed from the skin; the skin was soaked in normal saline and placed into the diffusion cell. The following solutions labeled with $^3$H in accordance with the standard method (Klimova et. al. 1993) were added into the donor chamber: complex of collagenolytic digestive protease from hydrobionts (Fermencol™, Table 3), Fe-superoxide dismutase from E. coli (Table 4) and fragments of rRNA 25-55 bases in length (Table 5).

TABLE 3

| Ammonium sulfate concentration in donor medium, M | Time of incubation, hrs | | | | |
|---|---|---|---|---|---|
| | 10 | 20 | 30 | 40 | 60 |
| | $^3$H-labeled marker in receptor medium, % from initial | | | | |
| 0 | 0.02 | 0.05 | 0.06 | 0.13 | 0.33 |
| 0.1 | 6.33 | 10.67 | 13.04 | 18.80 | 21.10 |
| 0.2 | 7.67 | 12.87 | 18.01 | 28.30 | 35.23 |
| 0.5 | 9.00 | 13.10 | 17.99 | 32.00 | 36.30 |
| 1.0 | 8.67 | 13.33 | 18.00 | 37.00 | 37.11 |

TABLE 4

| Ammonium sulfate concentration in donor medium, M | Time of incubation, hrs | | | | |
|---|---|---|---|---|---|
| | 10 | 20 | 30 | 40 | 60 |
| | $^3$H-labeled marker in receptor medium, % from initial | | | | |
| 0 | 0.01 | 0.05 | 0.07 | 0.11 | 0.34 |
| 0.1 | 5.31 | 10.00 | 12.06 | 17.99 | 20.11 |
| 0.2 | 5.67 | 12.56 | 17.90 | 27.60 | 35.11 |
| 0.5 | 7.80 | 10.81 | 16.94 | 31.00 | 35.30 |
| 1.0 | 7.67 | 10.33 | 16.74 | 31.00 | 35.11 |

TABLE 5

| Ammonium sulfate concentration in donor medium, M | Time of incubation, hrs | | | | |
|---|---|---|---|---|---|
| | 10 | 20 | 30 | 40 | 60 |
| | $^3$H-labeled marker in receptor medium, % from initial | | | | |
| 0 | 0.02 | 0.02 | 0.02 | 0.05 | 0.02 |
| 0.1 | 2.17 | 3.07 | 3.84 | 4.00 | 4.12 |
| 0.2 | 3.01 | 3.77 | 4.18 | 4.67 | 5.72 |
| 0.5 | 4.01 | 4.11 | 4.80 | 4.88 | 5.93 |
| 1.0 | 4.08 | 4.11 | 4.88 | 5.02 | 5.93 |

The data presented in Tables 3, 4 and 5 demonstrate that in the absence of ammonium sulfate, the rat skin permeability is very low, however, when ammonium sulfate at the concentration of >0.1 M is added to the donor solution, the skin permeability becomes 1.5 orders of magnitude higher. A further increase in the ammonium sulfate concentration in the donor solution up to 1 M insignificantly increases the diffusion of the radioactively labeled substrate.

We propose that superposition of two effects—"salting in" and "salting out"—occurs. At the concentration of ammonium sulfate of <0.2 M, the crucial factor in increasing the skin permeability is the hydration of keratinocytes that loosens SC by means of "swelling" its protein structural components and forms "routes" in the intercellular space by means of interstitial collagen loosening. At the concentration of ammonium sulfate of >0.2 M, a higher density of substrate molecules due to interaction between sulfate ions and positively charged amino acids, as well as dehydration of substrate molecules, is observed.

Similar results were obtained in the standard experiments with the Franz diffusion cell studying skin permeability for insulin and antibiotics: β-lactams (Amoxicillin, Carbenicillin), macrolides (erythromycin) and some substances that are the components of mesotherapy cocktails (vitamins, amino acids, low molecular weight hyaluronic acid).

Prior to the test, the rat skin was stabilized for 12 hours at 4° C. with the donor/receptor solutions (0.05 M tris-HCl, pH 7.5) containing ammonium sulfate at different concentrations. The donor solution had a 5 IU/ml or 0.25 mg/ml insulin concentration. The receptor solution aliquots were collected at different intervals and analyzed using HPLC.

The dependence of the total amount of insulin that passed through the skin on the ammonium sulfate concentration is demonstrated in FIG. 1. A further increase in the ammonium sulfate concentration does not influence the effectiveness of insulin diffusion from the donor solution to the acceptor solution. Apparently, it can be used in transdermal and transbuccal systems to create an ammonium sulfate gradient in all skin layers and subcutaneous tissues for the purposes of transdermal, intradermal and transbuccal delivery.

The experiments carried out by the authors demonstrated that the presence of ammonium sulfate in transdermally and transmucosally delivered substances leads to reversible modification of skin structural elements, hypodermis and mucosal membranes, thus forming routes through which biologically active macromolecules, can reach subcutaneous tissues and get into lymph and blood stream. Obviously, application of ammonium sulfate as the penetration enhancer can be highly effective for stable transdermal, intradermal and transbuccal delivery of a wide range of biologically active chemical compounds, such as peptides and proteins, hormones, vaccines and antibodies, oligonucleotides applied in antisense therapy, ribozymes, vectors for gene therapy, proteoglycans, lipoproteins, vitamins, and etc.

Positive results on the delivery of a range of substances including insulin and antibiotics through skin and mucous membranes were obtained in the experiments carried out in animals (rats and guinea pigs), as well as in the human studies for the intra-articular delivery of proteolytic enzymes.

Moreover ammonium sulfate stabilizes macromolecules that allows preparation of ready-to-use formulations, thereby eliminating the need to reconstitute the formulation before use, thus enhancing dosage precision and sterility.

The stability of proteases in presence of ammonium sulfate at a concentration of 0 to 80% saturation was determined by measuring the activity of samples stored at 45° C. for 0, 7, 21 and 45 days in 50 mM Tris-HCl buffer, pH 7.5, using azocasein hydrolysis (Table 6).

TABLE 6

The stability of the proteases in ammonium sulfate fractions after incubation at 45° C. in the assay buffer followed by determination of enzymatic activity.

| No. | Ammonium sulfate concentration in proteolytic/collagenolytic enzyme (Fermencol) solution, mM | Period of incubation at 45° C. for 0, 7, 21 and 45 days in the assay buffer. 0: Specific activity of collagenolytic enzyme (Fermencol) solution preparation toward Azocasein (Azocasein, Sigma-Aldrich, A2765), O.D. | 0: Specific activity of collagenolytic enzyme (Fermencol) solution preparation toward Azocasein (Azocasein, Sigma-Aldrich, A2765), % from initial | 7: Specific activity of collagenolytic enzyme (Fermencol) solution preparation toward Azocasein (Azocasein, Sigma-Aldrich, A2765), O.D. | 7: Specific activity of collagenolytic enzyme (Fermencol) solution preparation toward Azocasein (Azocasein, Sigma-Aldrich, A2765), % from initial |
|---|---|---|---|---|---|
| 1 | 0 | 11.00 | 100 | 10.52 | 95.64 |
| 2 | 1.0 | 10.89 | 100 | 10.79 | 99.10 |
| 3 | 2.0 | 10.67 | 100 | 10.70 | 100.00 |
| 4 | 3.2 | 10.56 | 100 | 10.64 | 100.00 |

| No. | Period of incubation at 45° C. for 0, 7, 21 and 45 days in the assay buffer. 21: Specific activity of collagenolytic enzyme (Fermencol) solution preparation toward Azocasein (Azocasein, Sigma-Aldrich, A2765), O.D. | 21: Specific activity of collagenolytic enzyme (Fermencol) solution preparation toward Azocasein (Azocasein, Sigma-Aldrich, A2765), % from initial | 45: Specific activity of collagenolytic enzyme (Fermencol) solution preparation toward Azocasein (Azocasein, Sigma-Aldrich, A2765), O.D. | 45: Specific activity of collagenolytic enzyme (Fermencol) solution preparation toward Azocasein (Azocasein, Sigma-Aldrich, A2765), % from initial |
|---|---|---|---|---|
| 1 | 9.23 | 83.91 | 7.65 | 69.55 |
| 2 | 10.65 | 97.82 | 10.65 | 97.82 |
| 3 | 10.54 | 98.78 | 10.71 | 100.00 |
| 4 | 10.70 | 100.00 | 10.62 | 100.00 |

When stored in 50 mM Tris-HCL buffer, pH 7.5 at 4° C. retained their full activity for at least one week; and when stored at −18° C., they retained their activity for a minimum of 6 months When the proteolytic enzymes were incubated in 50 mM Tris-HCL buffer, pH 7.5 at 45° C. without ammonium sulfate, they were stable for 60 mM; and when they were incubated at −18° C., they were stable for a minimum of 6 months.

With the ammonium sulfate concentration of 25% to 80% saturation, the proteolytic enzymes retained almost the same level of activity at 45° C. for at least 6 weeks.

This invention is not limited to the aforementioned examples. In general, all products and methods according to the invention can comprise, consist of, or essentially consist of any appropriate components or steps presented in this disclosure or known to one skilled in the art and such products or methods according to the invention can additionally or alternatively exclude any component or step or subject used in the product or method known from the prior art or which is not deemed to be required to achieve the technical result of this invention.

REFERENCES CITED

1. Ashok K. Tiwary, Bharti Sapra and Subheet Jain (2007). Innovations in Transdermal Drug Delivery: Formulations and Techniques Recent Patents on Drug Delivery & Formulation., v.1, pp. 23-36.
2. Bos J. D., Meinardi M. M. H. M (2000). The 500 Dalton rule for the skin penetration Jan D. Bos and of chemical compounds and drugs. Exp Dermatol.; v. 9, pp. 165-169.
3. Klimova O. A., Zolotarev Yu. A., Chebotarev V. Yu. (1993). The preparation of soft-tritium-labelled proteins and their application for the collagenolytic activity investigations. Biochem. Biophys. Res. Commun., v. 195. pp. 758-761.
4. Mandl I., MacLennan J. D., Howes E. L. (1953). Isolation and characterization of proteinase and collagenase from Cl. histolyticum. J. Clin Invest. December; v.32 (12), pp. 1323-1329.
5. Shiow-Fern Ng., Jennifer Rouse, Dominic Sanderson and Gillian Eccleston (2010). A Comparative Study of Transmembrane Diffusion and Permeation of Ibuprofen across Synthetic Membranes Using Franz Diffusion Cells Pharmaceutics; v.2(2), pp. 209-223.
6. Fernanda Sousa, Susana Jus, Anita Erbel, Vanja Kokol, Artur Cavaco-Paulo, G. M. Gubitz (2007). A novel metalloprotease from *Bacillus cereus* for protein fibre processing Enzyme and Microbial Technology; v. 40, pp. 1772-1781.

What is claimed is:

1. A method for increasing permeability of dermal tissue or mucosal tissue to at least one biologically active agent in a subject in need thereof, the method comprising contacting said dermal tissue or said mucosal tissue with an effective amount of the at least one biologically active agent in combination with a composition comprising ammonium sulfate, such that said permeability is increased; wherein penetration by said biologically active agent of said dermal tissue or said mucosal tissue occurs by passive diffusion and wherein the concentration of ammonium sulfate in the composition is between 0.1 M and 1 M.

2. A method of transdermally or transmucosally treating with at least one biologically active agent a subject in need of treatment with the at least one biologically active agent, the method comprising contacting dermal or mucosal tissue of said subject with at least one biologically active agent in combination with a composition comprising ammonium sulfate, such that said subject is treated; wherein penetration by said biologically active agent of said dermal tissue or said mucosal tissue occurs by passive diffusion and wherein the concentration of ammonium sulfate in the composition is between 0.1 M and 1 M.

3. The method of claim 1 or 2, wherein the biologically active agent is a biopolymer.

4. The method of claim 3, wherein the biologically active agent is an oligonucleotide, a protein, a peptide or an enzyme.

5. The method of claim 1 or 2, wherein the subject has diabetes and the biologically active agent is insulin.

6. The method of claim 1 or 2, wherein the subject has a skin wound or a scar and the biologically active agent is a proteolytic enzyme.

7. The method of claim 6, wherein the proteolytic enzyme is collagenase.

8. The method of claim 7, wherein the collagenase is represented by a complex of collagenolytic digestive proteases from hydrobionts.

9. The method of claim 6, wherein the skin wound or a scar results from a surgery, a burn, a frostbite, or acne.

10. The method of claim 1 or 2, wherein the dermal tissue is skin.

11. The method of claim 1 or 2, wherein the mucosal tissue is buccal tissue.

12. The method of claim 4, wherein the biologically active agent is superoxide dismutase.

13. The method of claim 1 or 2, wherein the one or more biologically active agent in combination with a composition comprising ammonium sulfate is administered dermally, bucally, sublingually, transmucosally, rectally, urethrally, vaginally, orally, instillationally or by inhalation.

14. The method of claim 13, wherein the one or more biologically active agent in combination with a composition comprising ammonium sulfate is administered orally in the form of a tablet, a capsule or a pellet.

15. The method of claim 13, wherein the one or more biologically active agent in combination with a composition comprising ammonium sulfate is administered topically in the form of a gel, an ointment, a liniment, a lotion, a cream, a pill, a powder, a suspension, an emulsion or a suppository.

16. The method of claim 13, wherein the one or more biologically active agent in combination with a composition comprising ammonium sulfate is administered by an intradermal injection.

17. The method of claim 1 or 2, wherein the one or more biologically active agent is used for mesotherapy and is a vitamin, a hormone, an amino acid or a hyaluronic acid.

* * * * *